US 6,571,131 B1

(12) United States Patent
Nguyen

(10) Patent No.: US 6,571,131 B1
(45) Date of Patent: May 27, 2003

(54) DEFLECTABLE CATHETER WITH MODIFIABLE HANDLE

(75) Inventor: Frank Nguyen, Chino Hills, CA (US)

(73) Assignee: Biosense Webster, Inc., Diamond Bar, CA (US)

( * ) Notice: Subject to any disclaimer, the term of this patent is extended or adjusted under 35 U.S.C. 154(b) by 246 days.

(21) Appl. No.: 09/710,210

(22) Filed: Nov. 10, 2000

(51) Int. Cl.$^7$ ................................................. A61N 1/05
(52) U.S. Cl. ..................................................... 607/122
(58) Field of Search ........................... 604/95; 600/374, 600/381; 607/122

(56) References Cited

U.S. PATENT DOCUMENTS

| | | | |
|---|---|---|---|
| 3,470,876 A | 10/1969 | Barchilon | 128/348 |
| 3,605,725 A | 9/1971 | Bentov | 128/2.05 R |
| 3,625,200 A | 12/1971 | Muller | 128/2.05 R |
| 4,191,196 A | 3/1980 | Bradley et al. | 128/733 |
| 4,233,991 A | 11/1980 | Bradley et al. | 128/733 |
| 4,685,457 A | 8/1987 | Donenfeld | 128/207.14 |
| 4,753,223 A | 6/1988 | Bremer | 128/4 |
| 4,826,087 A | 5/1989 | Chinery | 239/551 |
| 4,838,859 A | 6/1989 | Strassmann | 604/95 |
| 4,921,482 A | 5/1990 | Hammerslag et al. | 604/95 |
| 4,960,134 A | 10/1990 | Webster, Jr. | 128/786 |
| 4,998,916 A | 3/1991 | Hammerslag et al. | 604/95 |
| 5,019,090 A | 5/1991 | Pinchuk | 606/194 |
| 5,037,391 A | 8/1991 | Hammerslag et al. | 604/95 |
| 5,108,368 A | 4/1992 | Hammerslag et al. | 604/95 |
| RE34,502 E | 1/1994 | Webster, Jr. | 607/125 |
| 5,318,525 A | 6/1994 | West et al. | 604/95 |
| 5,325,845 A | 7/1994 | Adair | 128/4 |
| 5,334,145 A | 8/1994 | Lundquist et al. | 604/95 |
| 5,368,564 A | 11/1994 | Savage | 604/95 |
| 5,383,923 A | 1/1995 | Webster, Jr. | 607/125 |
| 5,397,304 A | 3/1995 | Truckai | 604/95 |
| 5,397,321 A | 3/1995 | Houser et al. | 606/41 |

(List continued on next page.)

FOREIGN PATENT DOCUMENTS

| | | |
|---|---|---|
| EP | 0 415 553 | 3/1991 |
| EP | 0 616 794 | 9/1994 |
| EP | 0 790 066 | 8/1997 |
| EP | 0868923 A2 | 10/1998 |
| EP | 1038545 A2 | 9/2000 |
| JP | 8112245 | 5/1996 |
| WO | 96/40344 | 12/1996 |

*Primary Examiner*—Scott M. Getzow
(74) *Attorney, Agent, or Firm*—Christie, Parker & Hale, LLP

(57) ABSTRACT

A deflectable catheter having a handle that can be modified pfor unidirectional or multidirectional deflection is provided. The catheter comprises an elongated, flexible tubular catheter body having proximal and distal ends and a lumen extending therethrough. A control handle is provided at the proximal end of the catheter body. The control handle comprises a handle body comprising an outer wall and a generally hollow interior, wherein the proximal end of the catheter body is fixedly attached to the handle body, a slidable puller wire anchor longitudinally movable within the interior of the handle body relative to the handle body and catheter body, a sleeve slidably mounted on the exterior of the handle body, and a selection pin fixedly attached to the sleeve and extending into the interior of the handle body proximal to the slidable puller wire anchor. In use, proximal movement of the sleeve and selection pin relative to the handle body causes the selection pin to contact the slidable puller wire anchor and move the slidable puller wire anchor proximally relative to the handle body and catheter body. The catheter further comprises a puller wire extending through the lumen of the catheter body and into the control handle. The proximal end of the puller wire is anchored to the slidable puller wire anchor, and the distal end of the puller wire is anchored in the distal end of the catheter body. In use, proximal movement of the slidable puller wire anchor relative to the catheter body results in deflection of the catheter body. For multidirectional deflection, the cather comprises a plurality of puller wires and a plurality of corresponding puller wire anchors.

15 Claims, 8 Drawing Sheets

U.S. PATENT DOCUMENTS

| | | | |
|---|---|---|---|
| 5,419,767 A | 5/1995 | Eggers et al. | 604/114 |
| 5,431,168 A | 7/1995 | Webster, Jr. | 128/658 |
| 5,441,483 A | 8/1995 | Avitall | 604/95 |
| 5,456,664 A | 10/1995 | Heinzelman et al. | 604/95 |
| 5,492,119 A | 2/1996 | Abrams | 128/642 |
| 5,507,725 A | 4/1996 | Savage et al. | 604/95 |
| 5,588,964 A | 12/1996 | Imran et al. | 604/95 |
| 5,626,136 A | 5/1997 | Webster, Jr. | 128/642 |
| 5,656,029 A | 8/1997 | Imran et al. | 604/95 |
| 5,656,030 A | 8/1997 | Hunjan et al. | 604/95 |
| 5,681,280 A | 10/1997 | Rusk et al. | 604/95 |
| 5,715,832 A | 2/1998 | Koblish et al. | 128/754 |
| 5,848,986 A | 12/1998 | Lundquist et al. | 604/22 |
| 5,987,344 A | 11/1999 | West | |
| 6,267,746 B1 | 7/2001 | Bumbalough | |

DEFLECTABLE CATHETER WITH MODIFIABLE HANDLE

FIELD OF THE INVENTION

This invention relates to a deflectable catheter, and more particularly to a catheter having a handle that can be modified to be used with unidirectional and multidirectional catheters.

BACKGROUND OF THE INVENTION

Steerable or deflectable tip cardiovascular catheters are useful in many applications, being a marked improvement over catheters with fixed tip curves. They are especially useful in the field of electrophysiology for performing radio frequency ablation of abnormal electrical pathways in the heart.

There are presently several useful designs of steerable tip catheters. One such steerable tip catheter is described in Reissue Pat. No. 34,502. The catheter has an elongated catheter body and tip portion that can be deflected into a semi-circle in one direction. In addition, the catheter body and tip portion can be rotated. Therefore by tip deflection, catheter rotation and catheter translation, i.e., lengthwise movement of the catheter, contact of the tip portion with most areas of a heart chamber may be made.

There are, however, structures and irregularity in the heart chambers that often make access difficult. In some cases it is necessary to reach around obstacles to contact a desired site. Moreover, it may be necessary to use a longer or shorter deflectable tip portion to reach a particular site and maintain adequate stable contact.

One early multidirectional deflectable tip catheter had a catheter body and tip with 5 lumens, i.e., a central lumen and four outer lumens disposed symmetrically around the central lumen. This catheter had four puller wires that extended through the outer lumens. The distal ends of the puller wires were attached to a ring at the tip and the proximal ends were attached to a "joy stick". The central lumen was open at its distal end and connected to a luer hub at its proximal end. This catheter had no reinforcement in its body or tip. It was not suitable for electrophysiology because it had effectively no torque transmission to the tip, which made tip rotation difficult. Moreover, the catheter body was subject to the same deflection as the tip, but to a lesser degree.

A more recent steerable catheter has a steerable tip that is controlled by a bendable control handle. Multiple puller wires connect the steerable tip to this control handle, which can be bent in any direction and can be thought of as a multiple ball joint with friction. The tip, once deflected, can be further deflected laterally by an internal stylette. The disadvantage of this catheter design is that the tip is very soft and has poor lateral stiffness due to the presence of the stylette, which cannot transmit torque effectively. Because of this, an electrode at the tip of the catheter cannot be held firmly against the myocardial wall.

Another recent steerable tip catheter comprises a deflectable tip that can be deflected in one direction by a puller wire and further deflected laterally by an internal stylette. The stylette can also be moved axially within the catheter to change the shape of the tip curvature. The disadvantage of this catheter design is that the lateral stiffness of the tip is dependent upon the stylette, which cannot transmit torque effectively. In a design wherein the tip is rotated by means of a stylette, it follows that the lateral stiffness of the tip must be less than that of the stylette alone. This is because some torque from the stylette is required to rotate the tip. Moreover, the stylet must be kept small to allow the catheter body and tip to bend and to be safe within the patient body and heart.

SUMMARY OF THE INVENTION

The invention is directed to a deflectable catheter having a conrol handle, wherein the control handle is preferably modifiable. The modifiable control handle permits the handle to be used with unidirectional and multidirectional catheters.

In one embodiment, the invention is directed to a deflectable catheter comprising an elongated, flexible tubular catheter body having proximal and distal ends and a lumen extending therethrough. A control handle is provided at the proximal end of the catheter body. The handle comprises a handle body having proximal and distal ends and comprising an outer wall and a generally hollow interior, wherein the proximal end of the catheter body is fixedly attached to the handle body. A slidable puller wire anchor is longitudinally movable within the interior of the handle body relative to the handle body and catheter body. A sleeve is slidably mounted on the exterior of the handle body. A selection pin is fixedly attached to the sleeve and extends into the interior of the handle body proximal to the slidable puller wire anchor. A puller wire having proximal and distal ends extends through the lumen of the catheter body and into the control handle. The proximal end of the puller wire is anchored to the slidable puller wire anchor, and the distal end of the puller wire is anchored in the distal end of the catheter body.

In use, proximal movement of the sleeve and selection pin relative to the handle body causes the selection pin to contact the slidable puller wire anchor and move the slidable puller wire anchor proximally relative to the handle body and catheter body. Proximal movement of the slidable puller wire anchor relative to the catheter body results in deflection of the distal end of the catheter body.

In a particularly preferred embodiment, the invention is directed to a deflectable catheter comprising an elongated, flexible tubular catheter body having proximal and distal ends and a lumen extending therethrough. A control handle is provided at the proximal end of the catheter body. The handle comprises a handle body having proximal and distal ends and comprising a barrel at the handle body's proximal end, the barrel having proximal and distal ends, an outer wall having a plurality of longitudinal slots therein, and a generally hollow interior, and a nose piece at the handle body's distal end, the nose piece having proximal and distal ends, an outer wall, and a generally hollow interior. The handle body further comprises a sectioned insert permanently or removably mounted, at least in part, in the distal end of the barrel and permanently or removably attached to the nose piece. The sectioned insert comprises an axis, a plurality of fins extending from the axis, thereby forming a plurality of sections, and a central groove distal to the fins. The longitudinal slots in the outer wall of the barrel correspond in number and location to the sections formed by the sectioned insert. The handle further comprises a plurality of slidable puller wire anchors, wherein each puller wire anchor is provided in one of the sections of the sectioned insert and is longitudinally movable within the interior of the handle body relative to the handle body and catheter body.

A sleeve is slidably and rotatably mounted on the exterior of the handle body. A selection pin is fixedly attached to the sleeve and extends into the interior of the handle body proximal to the slidable puller wire anchor. The catheter further comprises a puller wire having proximal and distal ends and extending through the lumen of the catheter body and into the control handle. The proximal end of the puller wire is anchored to one of the slidable puller wire anchors, and the distal end of the puller wire is anchored in the distal end of the catheter body. Additional puller wires can be provided that are attached at their proximal ends to the other puller wire anchors.

In use, rotation of the sleeve relative to the handle body causes the selection pin to rotate within the central groove. Proximal movement of the sleeve and selection pin relative to the handle body causes the selection pin to contact one of the slidable puller wire anchors and move that slidable puller wire anchor proximally relative to the handle body and catheter body. Proximal movement of the slidable puller wire anchor attached to the puller wire relative to the catheter body results in deflection of the catheter body.

DESCRIPTION OF THE DRAWINGS

These and other features and advantages of the present invention will be better understood by reference to the following detailed description when considered in conjunction with the accompanying drawings wherein:

FIG. 3 is a longitudinal cross-sectional view showing a preferred means of joining a catheter tip section to a body.

FIG. 4 is a longitudinal cross-sectional view of the catheter tip section showing a preferred means for anchoring the puller wires.

DETAILED DESCRIPTION OF THE INVENTION

Figure 1:
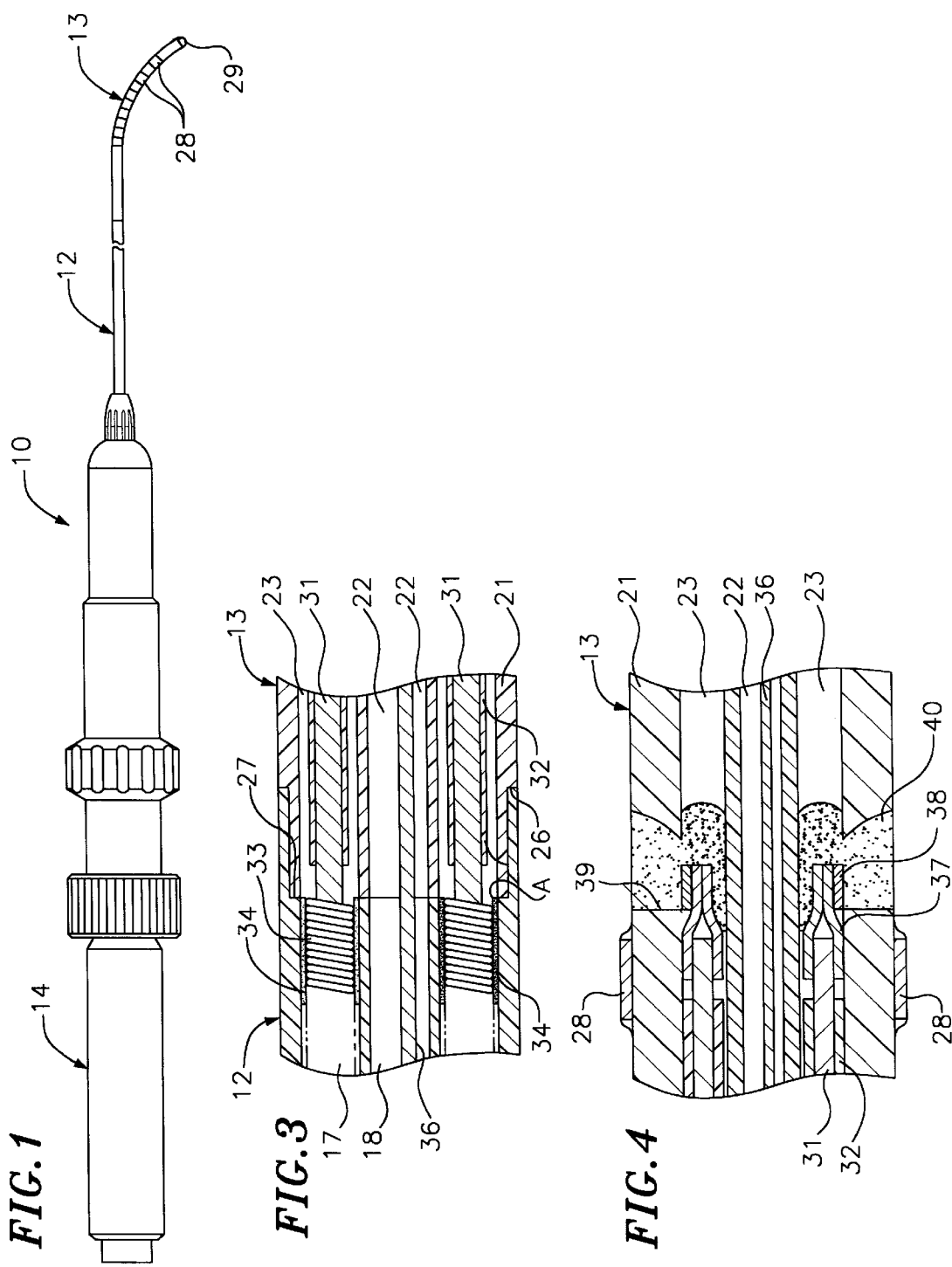
FIG. 1 is a side view showing a preferred catheter constructed in accordance with the present invention.

A particularly preferred deflectable electrode catheter constructed in accordance with the present invention is shown in FIG. 1. As shown in FIG. 1, the catheter 10 comprises an elongated catheter body 12, a deflectable tip section 13 and a control handle 14.

Figure 2:
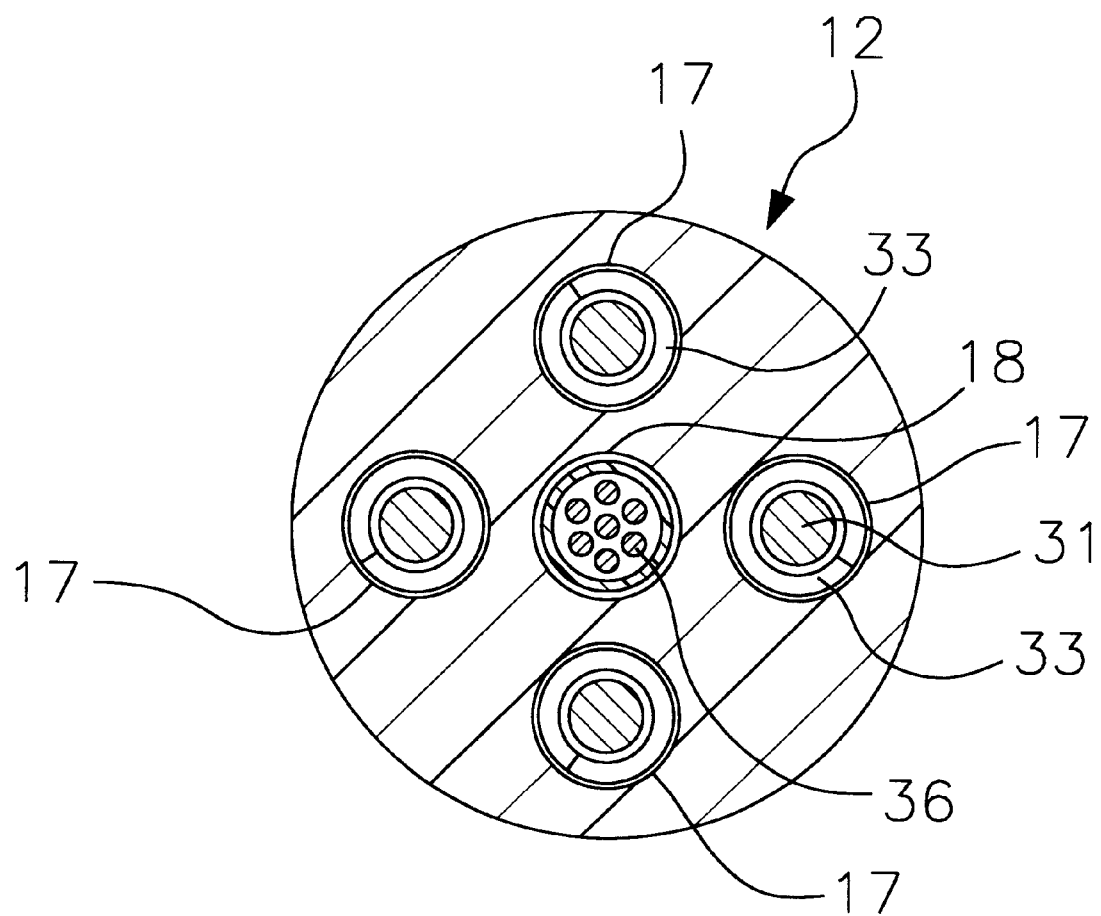
FIG. 2 is a transverse cross-sectional view of one embodiment of a catheter body showing the lumen arrangement.

With reference to FIG. 2, the catheter body 12 comprises an elongated tubular construction having four outer lumens 17 and a central (axial) lumen 18. The outer lumens 17 are arranged symmetrically into quadrants about the central lumen 18. The diameter of the lumens may vary as desired. In a preferred embodiment, each of the lumens has a diameter of about 0.018 inch. The catheter body 12 is made of any suitable non-toxic material such as polyurethane. The catheter body 12 is preferably reinforced with at least one layer of a braided mesh of stainless steel or the like to increase its torsional stiffness. The overall length and diameter of the catheter may vary according to the application. A presently preferred catheter has an overall length of about 48 inches and an outer diameter of about 0.09 inches.

With reference to FIG. 4, the catheter tip section 13 comprises a short section of flexible tubing 21 having a central tip lumen 22 and four outer tip lumens 23 (of which two are shown in FIG. 4) positioned symmetrically about the central lumen 22 in an arrangement corresponding to the lumens 17 and 18 of the catheter body 12. The tubing 21 is made of a suitable material and is preferably more flexible than the catheter body 12. A presently preferred material for the catheter tip section 13 is polyurethane reinforced with a metallic braided mesh, similar to that used in the catheter body 12 to impart the same high torque characteristics without appreciably increasing its bending stiffness. The diameter of the tip section 13 is preferably the same as or slightly smaller than that of the catheter body 12. In a preferred embodiment, the tip section 13 has a diameter of about 0.08–0.09 inches and a length of about 3 inches.

A preferred means for attaching the catheter tip section 13 to the catheter body 12 is illustrated in FIG. 3. The proximal end of the tip section 13 comprises an outer circumferential notch 26 and the distal end of the catheter body 12 comprises an inner circumferential notch 27. The notches 26 and 27 are sized such that the proximal end of the tip section 13 fits snugly into the distal end of the catheter body 12. The catheter tip section 13 is then fixedly attached to the catheter body by polyurethane glue or the like, creating a seam on the outer surface of the catheter at the junction between the tip section and the catheter body 12. The central tip lumen 22 and outer tip lumens 23 are aligned with and communicate with the central lumen 18 and outer lumens 17 of the catheter body 12, respectively. As would be recognized by one skilled in the art, the central lumen 18 and outer lumens 17 of the catheter body 12 could be replaced by a single axial lumen (not shown) that is in communication with all of the lumens 22 and 23 of the tip section 13.

Along the length of the tip section 13 are mounted a plurality of ring electrodes 28. The length of each ring electrode 28 is not critical, but preferably ranges from about one to about four millimeters. The ring electrodes 28 are spaced apart a distance of about 2 to 4 millimeters. A tip electrode 29 is mounted at the distal end of the tip section 13. As would be recognized by one skilled in the art, the presence and number of ring electrodes 28 and the tip electrode 29 can vary based on the specific application for which the catheter is to be used. As would be recognized by one skilled in the art, other electrode arrangements could be provided at the distal end of the catheter.

Each electrode 28 and 29 is connected to a separate lead wire 36, and the lead wires extend through the central lumens 18 and 22. The proximal ends of lead wires 36 are connected to an appropriate jack or other connector, which can be plugged into or otherwise connected to a suitable monitor or a source of ablation energy, e.g., radio frequency energy, depending on the application for which the catheter is to be used.

Connection of the lead wires 36 to the ring electrodes 28 and tip electrode 29 is accomplished by any suitable technique. For example, for a ring electrode 28, a small hole is made through the wall of the tip section 13 and into the central lumen 22. Such a hole may be created, for example, by inserting a needle through the tip section wall and heating the needle sufficiently to form a permanent hole. A lead wire 36 is then drawn through the hole using a microhook or the like. The end of the lead wire 36 is then stripped of any coating and soldered or welded to the underside of the ring electrode 28, which is then slid into position over the hole and fixed in place with polyurethane glue or the like. For the tip electrode 29, the distal end of a lead wire 36 can be soldered, welded or otherwise attached in a blind hole (not shown) in the tip electrode.

A mechanism is provided for steering and deflecting the tip section 13. Specifically, four puller wires 31 are provided. Each puller wire 31 extends from the control handle 14 through a corresponding outer lumen 17 in the catheter body 12 and into an aligned outer lumen 23 of the tip section 13. Each puller wire 31 is made of any suitable metal, such as stainless steel or Nitinol, and is preferably coated with Teflon®, Kevlar®, carbon fiber or the like for lubricity. Each puller wire 31 has a diameter preferably from about 0.006 to about 0.010 inch. Within the tip section 13, a plastic, preferably Teflon®, sheath 32 prevents the puller wire from cutting into the wall of the tip section when the tip section is deflected, as shown in FIG. 4. At its distal end, the puller wire 31 extends beyond the plastic sheath 32.

With reference to FIG. 2, within the catheter body 12, four compression coil 33 are provided, each in surrounding relation to a corresponding puller wire 31. Each compression coil 33 extends through a corresponding outer lumen 17. Each compression coil 33 is made of a suitable metal, e.g., stainless steel, which is tightly wound on itself to provide flexibility, i.e., bending, but to resist compression. The inner diameter of each compression coil 33 is selected to be slightly larger than the diameter of the puller wire 31. For example, when the puller wire 31 has a diameter of about 0.007 inch, a compression coil 33 having an inner diameter of about 0.008 inch is presently preferred. The outer diameter of the compression coil 33 is likewise slightly smaller than the diameter of the outer lumen 17 through which it extends.

Each compression coil 33 is fixedly attached to the proximal and distal ends of the catheter body 12 by polyurethane glue or the like. The glue may be applied through a syringe or the like to the outer circumference of the ends of the compression coil 33, for example as shown in FIG. 3 at location A. Glue applied to this location wicks inwardly between the compression coil 33 and the wall forming the lumen 17. Upon curing, a glue joint 34 is formed. Alternatively, the glue may be applied by means of a syringe or the like through a hole between the outer surface of the catheter body 12 and the outer lumen 17. Such a hole may be formed for example by a needle or the like which punctures the catheter body wall and is heated sufficiently to form a permanent hole. The glue is introduced through the hole to the outer surface of the compression coil 33 and wicks around the outer circumference to form a glue joint 34 about the entire circumference of the compression coil 33. If the latter method is used, it is understood that the distal end of the compression coil 33 could be located in the proximal portion of the tip section 13 rather from at the distal end of the catheter body 12. Such an embodiment provides added support to the juncture of the catheter body 12 and tip section 13.

Figure 5A:
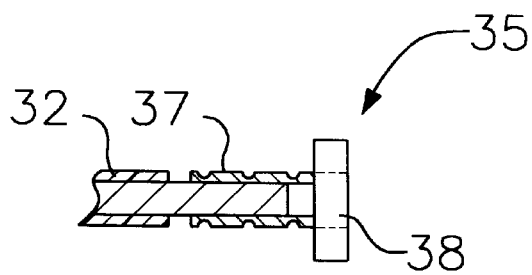
FIGS. 5A and 5B are longitudinal cross-sectional views of a preferred puller wire T-bar anchor.
Figure 5B:
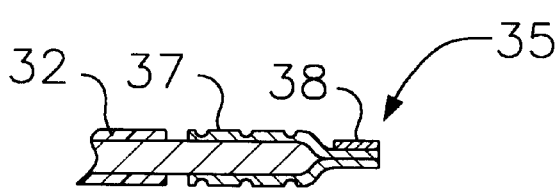

Each puller wire 31 is anchored in the tip section 13, preferably to the side of the tip section 13 or to the tip electrode 29. To anchor a puller wire to the side of the tip section 13, an anchor 35 is fixedly attached to the distal end of the puller wire 31, as shown in FIGS. 4, 5A and 5B. In a preferred embodiment, the anchor is formed by a metal tube 37, e.g., a short segment of hypodermic stock, which is fixedly attached, e.g., by crimping, to the distal end of the puller wire 31. The tube 37 has a section that extends a short distance beyond the distal end of the puller wire 31. A cross-piece 38 made of a small section of stainless steel ribbon or the like is soldered or welded in a transverse arrangement to the distal end of the tube section 37, which is flattened during the operation. This creates a T-bar anchor 35. A notch 39 is created in the side of the tip section 13, resulting in an opening into the outer lumen 23 into which the puller wire 31 extends. The anchor 35 lies partially within the notch 39. Because the length of the ribbon forming the cross-piece 38 is longer than the diameter of the opening into the lumen 23, the anchor 35 cannot be pulled completely into the lumen 23. The notch 39 is then sealed with polyurethane glue 40 or the like to give a smooth outer surface.

Figure 6A:
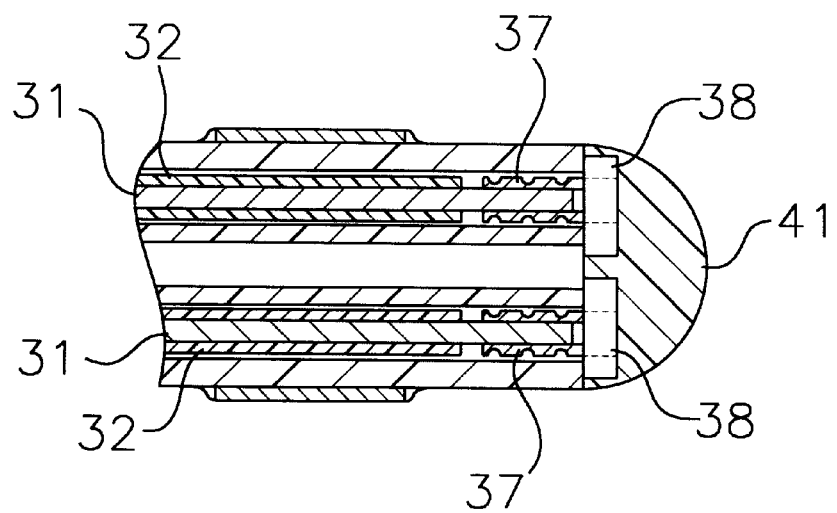
FIG. 6A is a longitudinal cross-sectional view of an arrangement for anchoring a puller wire in the distal end of the tip section.
Figure 6B:
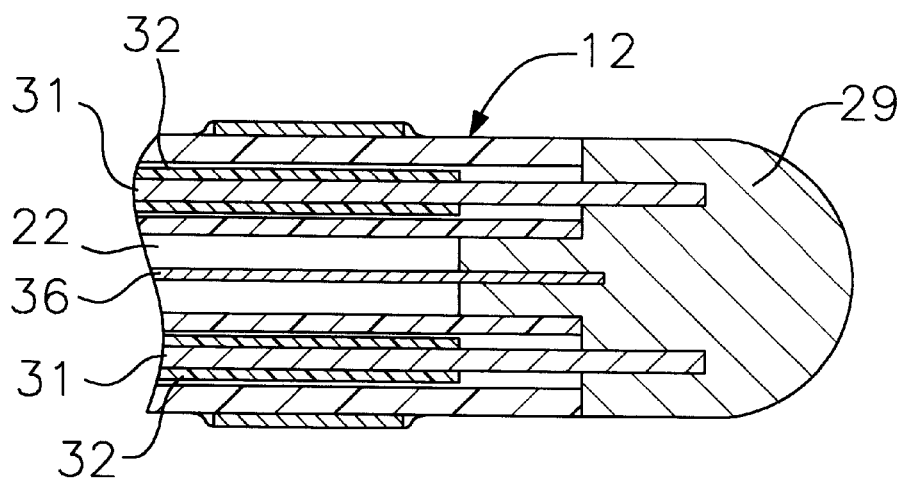
FIG. 6B is a longitudinal cross-sectional view of an arrangement for anchoring a puller wire to a tip electrode.

Alternatively, the puller wires 31 may be anchored at the distal end of the tip section 13 as shown in FIG. 6A. In this arrangement, each puller wire 31 extends to the distal end of the corresponding outer lumen 23, with the anchor 35, which is attached to the end of the puller wire, lying beyond the end of the lumen 23. The anchor 35 is fixed in this position by a polyurethane cap 41, which also acts to seal the distal end of the tip section 13. Because the cross-piece 38 is longer than the diameter of the outer lumen 23, the anchor 35 cannot be pulled back into the outer lumen when the tip section 13 is deflected. This alternative anchoring method is useful when there is no tip electrode 29. If a tip electrode 29 is present, the puller wires 31 may be anchored to the tip electrode 29, e.g., by solder, as shown in FIG. 6B.

Preferably, the four puller wires 31 are oriented 90° from each other. In one embodiment, all of the puller wires 31 have their distal ends anchored at the same distance from the distal end of the tip section 13. In an alternate embodiment, the distal ends of one or more of the puller wires 31 are anchored at a location distal to the distal ends of other puller wires. For example, two puller wires 31 can be anchored to the wall of the tip section 13, and the other two puller wires can be anchored to the tip electrode 29. The distance between the distal end of a compression coil 33 and the anchor site of the corresponding puller wire 31 in the tip section 13 determines the curvature of the tip section in the direction of that puller wire. It is understood that each of the four puller wires 31 may be anchored at the same location along the length of the tip section 13, in which case the curvatures of the tip section in all directions are the same and the tip section can be made to deflect in any direction without rotation of the catheter body 12. Alternatively, the puller wires 31 may have their distal ends anchored at three or four different locations along the length of the tip section 13. In the latter case, each quadrant has a distinct curvature. By rotating the catheter body 12, which is possible due to the high torque shaft, a physician may use any of the four curvatures or combinations thereof as desired.

Figure 7:
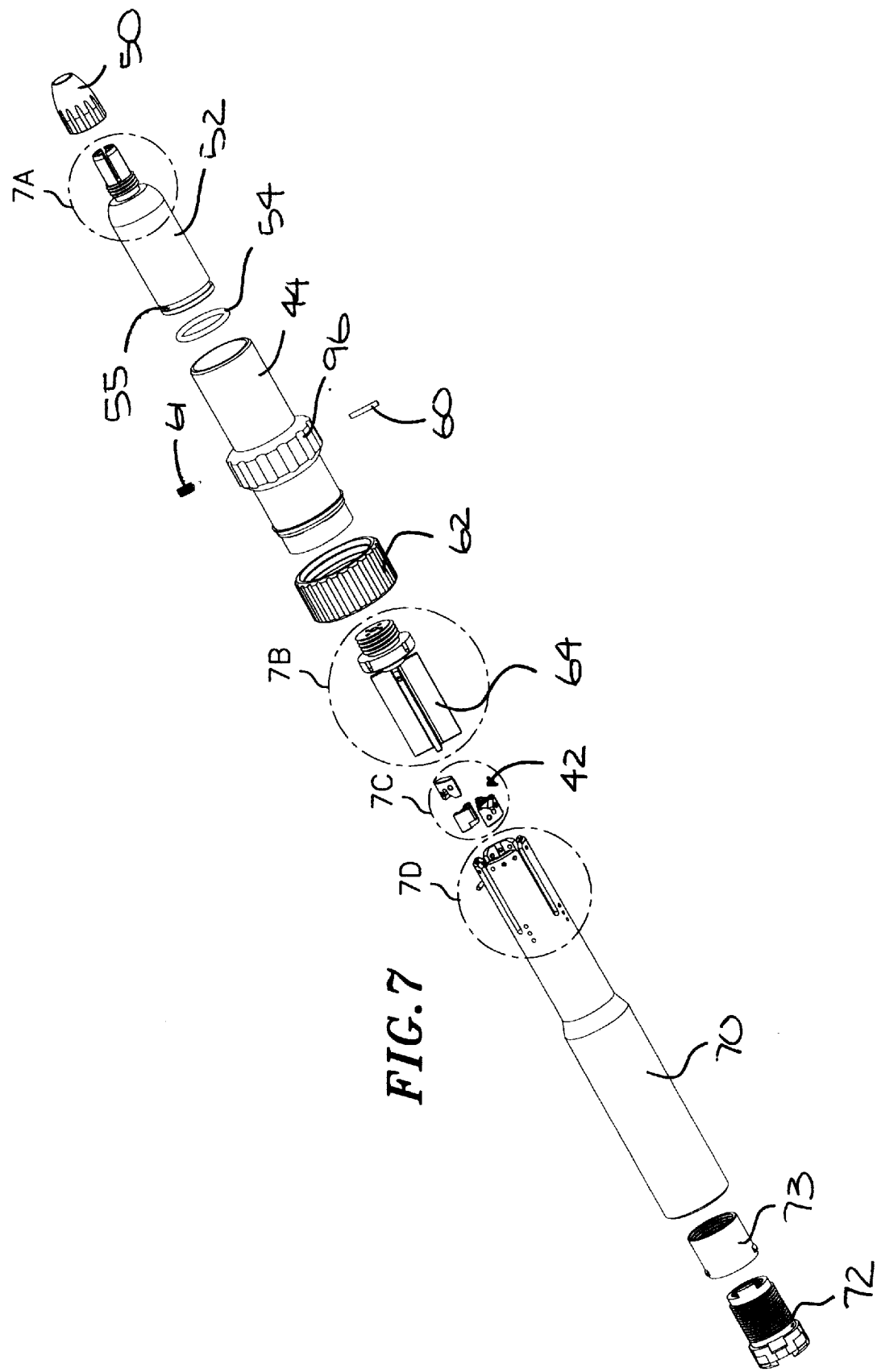
FIG. 7 is an exploded longitudinal view of a control handle in accordance with the invention.

Longitudinal movement of the puller wires 31 is controlled by the control handle 14. With reference to FIGS. 1 and 7, the control handle 14 comprises a handle body 40, four slidable puller wire anchors 42 within the handle body, and a sleeve 44 rotatably and slidably mounted on the handle body.

In the depicted embodiment, the handle body 40 comprises a barrel 70 at its proximal end and a nose piece 52 at its distal end. The barrel 70 comprises an outer wall and a generally hollow interior in which a sectioned insert 64 is removably mounted, at least in part. The nose piece 52 similarly comprises an outer wall and a generally hollow interior. Both the barrel 70 and the nose piece 52 are generally cylindrically-shaped. The sectioned insert 64, described in more detail below, has a threaded distal section 81 for mating with interior threads (not shown) inside the proximal end of the nose piece 52. Accordingly, when the handle body 40 is assembled, the barrel 70 is indirectly attached to the nose piece 52 by way of the sectioned insert 64 removably mounted in the barrel. The sectioned insert 64 could alternatively be fixedly mounted in the barrel 40, although such a design provides less flexibility in the manufacture of the catheter, as discussed further below.

Figure 7A:
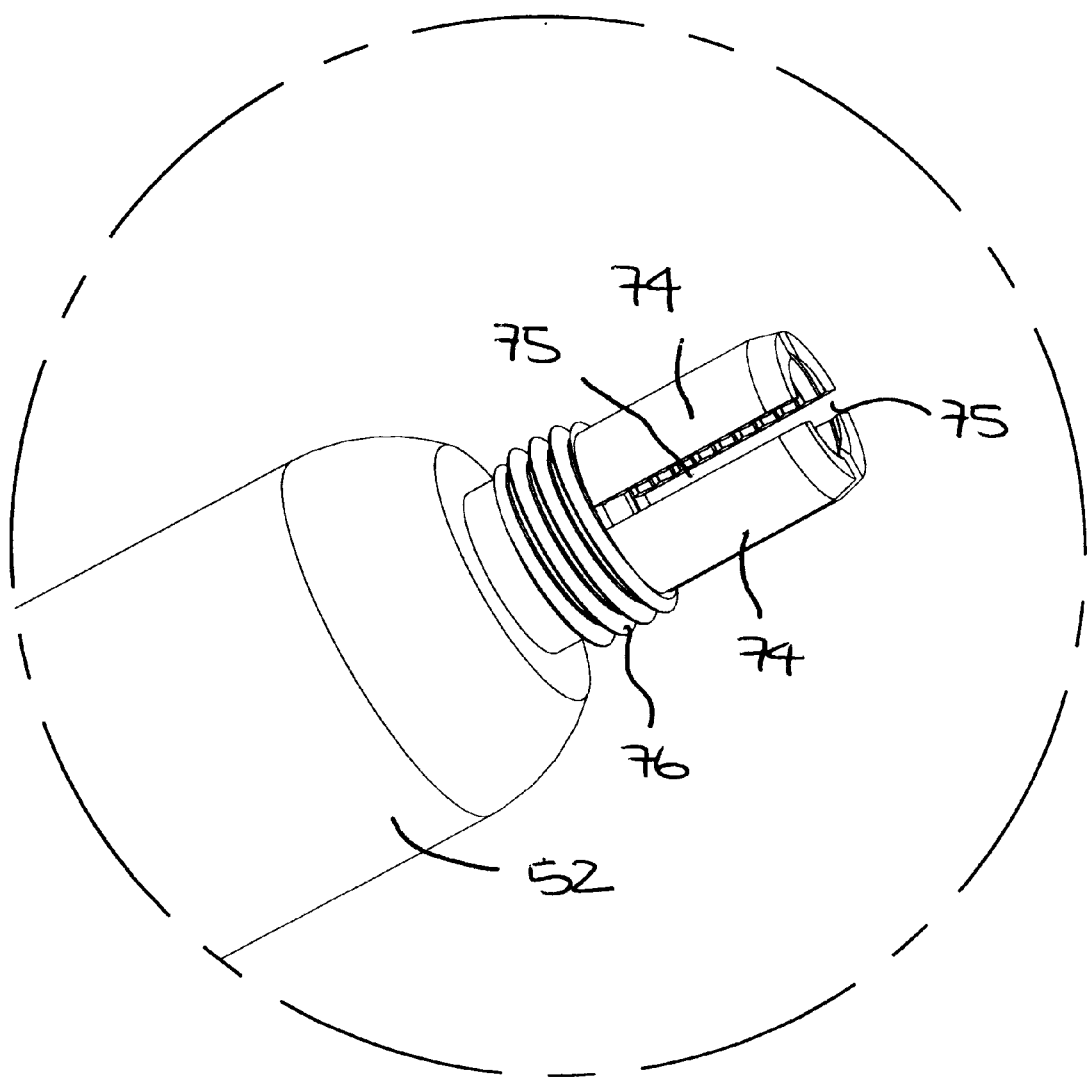
FIG. 7A is an enlarged view of the nose piece depicted in FIG. 7.

The proximal end of the catheter body 12 is fixedly attached to the handle body 40 by any suitable method. In the depicted embodiment, the proximal end of the catheter body is fixedly attached to the distal end of the nose piece 52. As best shown in FIG. 7A, the distal end of the nose piece 52 comprises four compressible sections 74 with longitudinal slits 75 therebetween arranged in a generally-cylindrical relationship, and a series of threads 76 proximal to the compressible sections. The proximal end of the catheter body 12 is inserted into the distal end of the nose piece 52. An end cap 50 is placed over the compressible sections 74 and catheter body 12 and screwed onto the nose piece 52 by means of interior threads (not shown) in the end cap that interact with the threads 76 on the nose piece. The end cap 50 compresses the compressible sections 74 against the catheter body 12, holding the catheter body tightly in place. The lead wires 36 that extend through the catheter body 12 also extend through the handle body 40 and terminate in their proximal ends at a connector 72, which is attached to the handle body via an adapter 73. The four puller wires 31 that extend through the catheter body 12 extend through the nose piece 52 and are anchored to the four puller wire anchors 42 in the handle body 40, as described in more detail below.

Figure 7B:
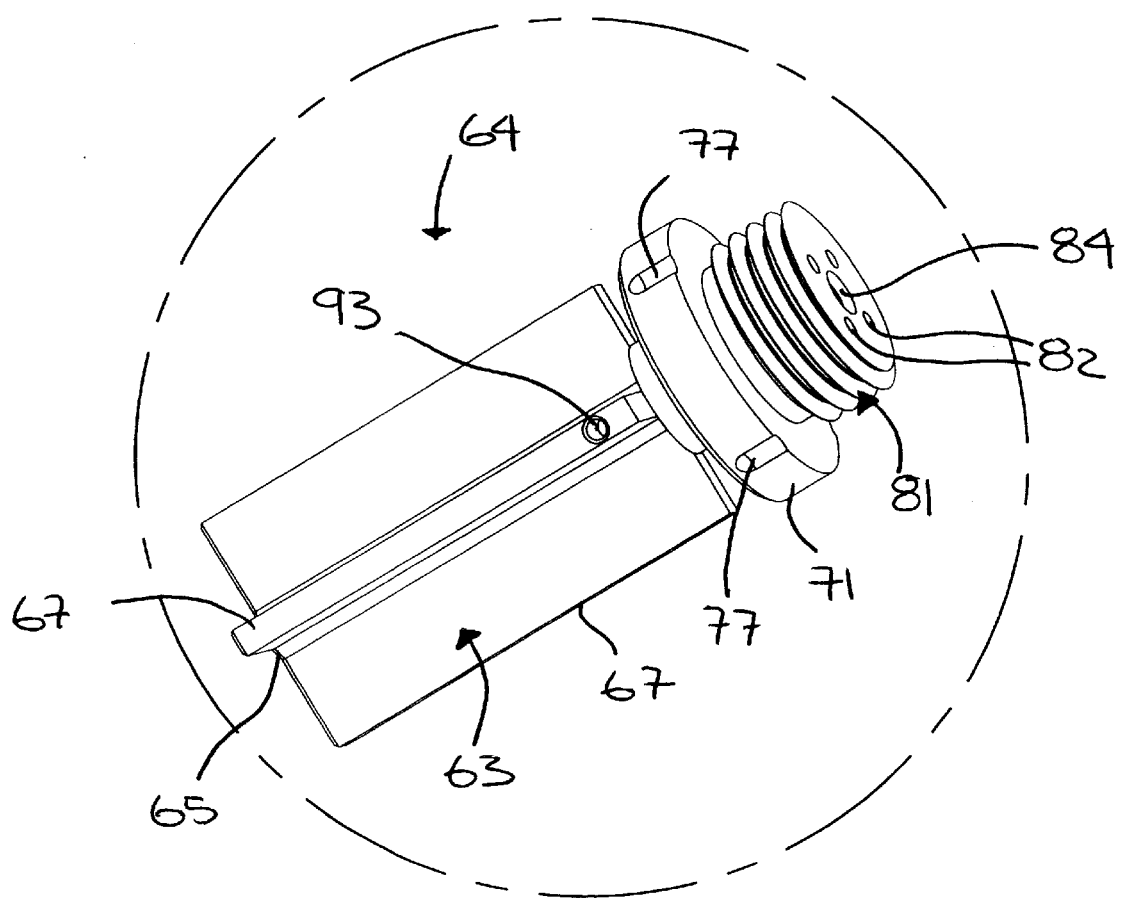
FIG. 7B is an enlarged view of the sectioned insert depicted in FIG. 7.

As best shown in FIG. 7B, the sectioned insert 64 has a threaded distal section 81, discussed above, and a proximal section 63 comprising an axis 65 and four fins 67 extending therefrom. Between the distal section 81 and the proximal section 63 are a central groove 69 for receiving a selection pin 60, described in more detail below, and a circumferential ridge 71 distal the central groove and proximal the distal section. The distal section 81 of the sectioned insert 64 has four puller wire holes 82 through which the four puller wires 31 pass. The distal section 81 and the axis 65 of the proximal section 63 include a central passage 84 through which the lead wires 36 pass from the catheter body 12. The four fins 67 of the proximal section 63 are located at 90 degree angles relative to one another, thereby forming four quadrants. Slidably disposed within each quadrant of the proximal section 63 is a slidable puller wire anchor 42. Each puller wire 31 is anchored at its proximal end to a different corresponding puller wire anchor 42 by any suitable method, as discussed further below.

In the depicted embodiment, the sectioned insert 64 is removably mounted in the distal end of the barrel 70 with four pins (not shown). The sectioned insert 64 has a pin hole 93 provided on the outer edge of each fin 67. The barrel has four pin holes 92 extending through the distal end of its outer wall, as shown in FIG. 7D. The barrel pin holes 92 are located about the circumference of the barrel 70 to correspond in position to the insert pin holes 93. Thus, the four pins are inserted through the insert pin holes 93 and barrel pin holes 92 to maintain the sectioned insert 64 in place in the barrel 70. This arrangement allows the sectioned insert 64 to be removed from the barrel to reposition the slidable puller wire anchors 42 within the handle body 40 if desired, as described in more detail below. When the sectioned insert 64 is fixed in place in the barrel 70, the central groove 69 of the insert is positioned just proximal the distal end of the barrel.

Figure 7C:
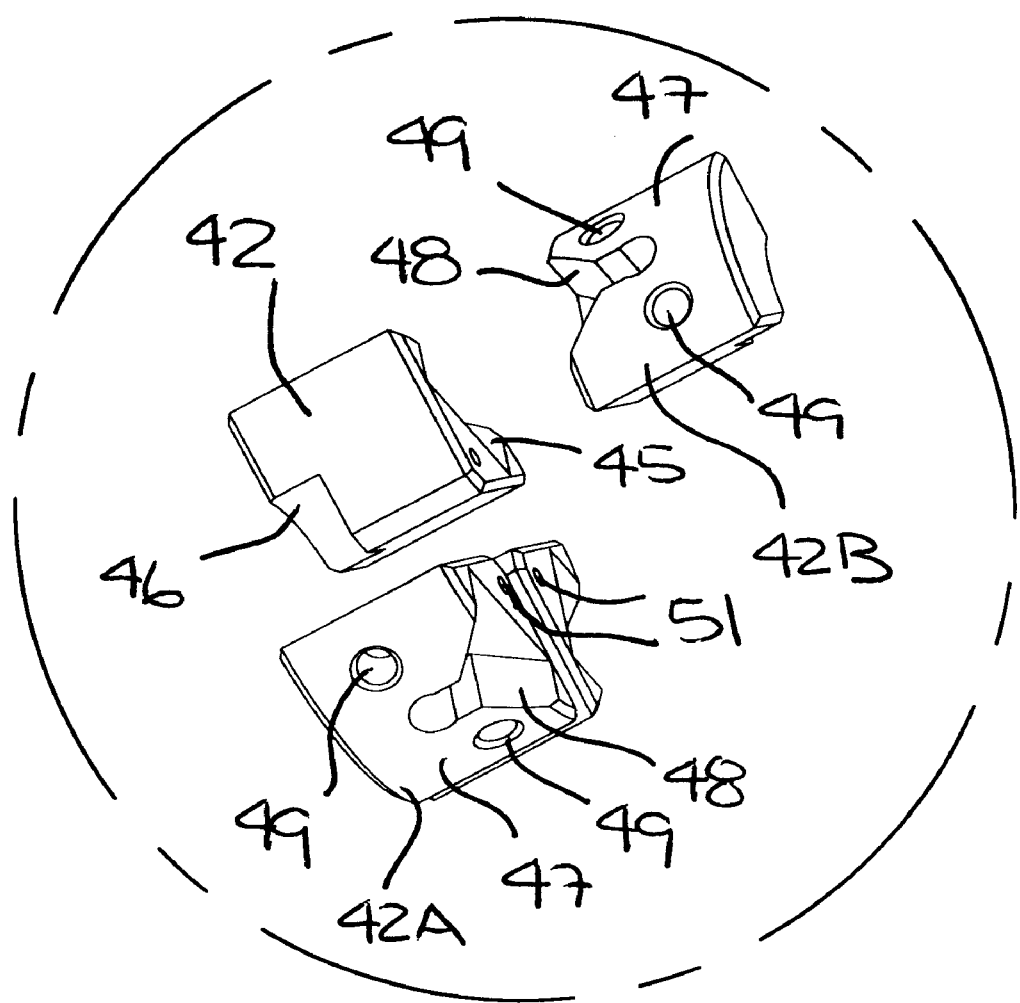
FIG. 7C is an enlarged view of the slidable puller wire anchors depicted in FIG. 7.
Figure 7D:
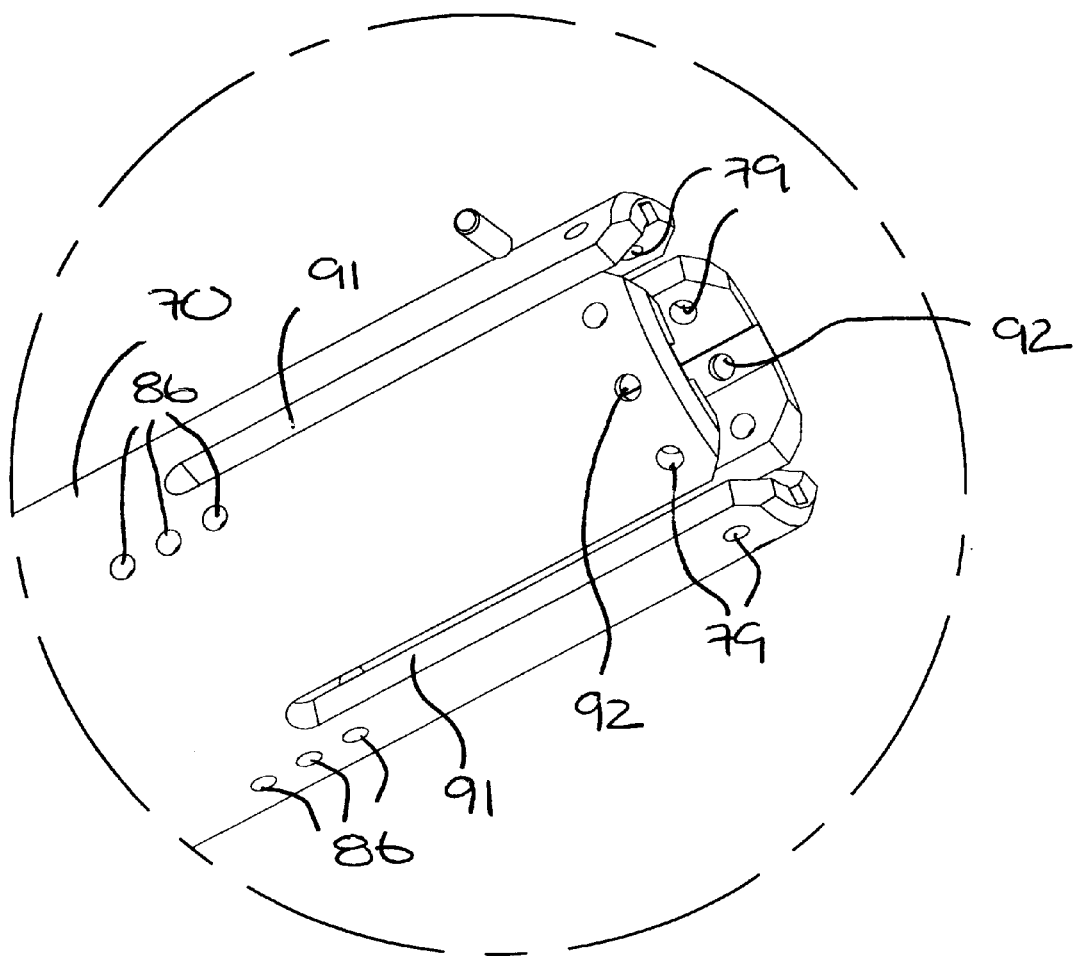
FIG. 7D is an enlarged view of the distal end of the barrel depicted in FIG. 7.

In a particularly preferred embodiment, as best shown in FIG. 7C, each slidable puller wire anchor 42 is generally pie-shaped having a generally open end 45, a generally closed end 46, and an outer wall 47. The outer wall 47 has a generally V-shaped groove 48 and two mounting holes 49, the purposes of which are described in more detail below. Each puller wire anchor 42 further includes a puller wire hole 51 extending longitudinally therethrough.

The sleeve 44 is rotatably and slidably mounted on the handle body 40 between the barrel 70 and the nose piece 52. An O-ring 54 is provided in a groove 55 at the distal end of the nose piece 52 to provide a seal between the nose piece and the sleeve 44. The sleeve 44 comprises a rotation knob 96 mounted thereon through which a selection pin 60 extends radially inward. The selection pin 60 is provided to contact one of the slidable puller wire anchors 42 and move that anchor proximally relative to the handle body 40 for deflection of the tip section 13. The length of the sleeve 44 is not critical, but is preferebly sufficiently long to accomodate the rotational knob 96, which is preferably of a size to provide ease of use to the physician, and to accomodate a camlock ring 62, discussed further below.

Specifically, four longitudinal slots 91 are provided through the distal end of the outer wall of the barrel 70 for receiving the selection pin 60. Each longitudinal slot 91 corresponds to one of the four quadrants formed by the sectioned insert 64. In the depicted embodiment, each longitudinal slot 91 is provided at the middle of the quadrant, i.e., at a position midway between the two fins 67 that form the quadrant.

In use, the physician turns the rotation knob 96 and sleeve 44 about the handle body 40 to align the selection pin 60 with one of the four slidable puller wire anchors 42. The sleeve 44 can only be rotated about the handle body 40 when the handle is in the neutral position, i.e., when the tip section 13 is not deflected. When the handle is in the neutral position, the selection pin 60 is aligned with the central groove 69 of the sectioned insert 64, which, as described above, is positioned just distal to the distal end of the barrel 70. Accordingly, the selection pin 60 is not rotationally restricted within the central groove 69.

Once the selection pin 60 is rotated to be in alignment with a desired puller wire anchor 42, the sleeve 44 and selection pin are pushed proximally relative to the handle body 40 to contact the selection pin with the desired puller wire anchor. The selection pin 60 fits into the V-shaped groove 48 of the anchor 42, and further proximal movement of the selection pin in the corresponding longitudinal slot 91 moves the anchor proximally. As the puller wire anchor 42 moves proximally relative to the handle body 40 (and thus catheter body 12), the puller wire 31 anchored to that puller wire anchor also moves proximally relative to the catheter body, thereby deflecting the tip section 13 in the direction of the side of the tip section to which that puller wire is anchored. Once the selection pin 60 is moved proximally into the longitudinal slot 91, rotational movement of the pin and sleeve 44 is prohibited. By this design, simultaneous movement of multiple puller wires 31 is prevented because the selection pin 60 causes proximal movement of only one puller wire anchor 42 relative to the handle body 40 at a time.

A mechanism is provided to adjustably limit the distance that each puller wire anchor 42 can move proximally relative to the handle body 40, thereby dictating the extent of curvature of the tip section 13 upon movement of the puller wire 31 attached to that anchor. The mechanism comprises four series of limiting holes 86 in the outer wall of the barrel 70, each series corresponding in position to one of the four puller wire anchors 42. A removable limiting pin (not shown) is provided in one of the limiting holes 86 of each series to limit the distance that the puller wire anchor 42 corresponding to the series can move proximally. The limiting hole 86 in which each limiting pin is placed is determined based on the desired curvature of the tip section 13. As would be recognized by one skilled in the art, the above-described adjustable limiting mechanisms could be replaced with a single permanent limiting mechanism for each anchor 42.

Once the puller wire anchor 42 and corresponding puller wire 31 have been moved proximally relative to the handle body 40 (and thus catheter body 12), thereby deflecting the tip section 13, the sleeve 44 can be locked in place on the barrel 70 to prevent the tip section from straightening if the user releases control handle. Specifically, a camlock ring 62 is mounted in surrounding relation on the distal end of the sleeve 44, which is provided over the proximal end of the barrel 70. The proximal end of the sleeve 44 has a variable outer diameter, so that it has one section of its outer circumference that is thicker than the remainder of the outer circumference, and a short longitudinal groove (not shown). The camlock ring 62 has a corresponding variable inner diameter. When the camlock ring 62 is turned about the sleeve 44, the region of the camlock ring with a decreased inner diameter comes into contact with the region of the sleeve with the increased outer diameter, thereby compressing the sleeve against the barrel 70. This compression locks the sleeve 40 against the barrel 70. When the user wants to release the deflection of the tip section 13, the user turns the camlock ring 62 in the opposite direction, thereby loosening the sleeve 44 on the barrel 70. The user can then slide the sleeve 44 distally relative to the handle body 40 to the neutral position, thereby straightening the tip section 13.

If the user desires to deflect the tip section 13 in a different direction and/or to form a different curve, he then rotates the sleeve 44 and selection pin 60 about the handle body 40 to align the selection pin with a different puller wire anchor 42. The above-described steps are then repeated for that puller wire anchor 42. However, as discussed above, the selection pin 60 can only be rotated when the sleeve 44 is in the neutral position (i.e., when the tip section 13 is straight), because when the sleeve is proximal the neutral position, the selection pin is positioned within a longitudinal slot 91. However, when the sleeve 44 is in the neutral position, the sleeve and selection pin 60 can be rotated a full 360 degrees in the central groove 69 of the sectioned insert 64 because there is nothing blocking rotation of the selection pin in this embodiment.

The sleeve 42 further comprises a ball plunger 61 for tactile feel by a user of the location and orientation of the sleeve relative to the barrel 70 and puller wire anchors 42. The ball plunger 61 projects inward from the rotation knob 96 and is rotated about the circumferential ridge 71 of the sectioned insert 64. Four detents 77 are provided on the circumference of the circumferential ridge 71, each detent 77 corresponding to a different quadrant of the sectioned insert 64 and to a different puller wire anchor 42. When the sleeve 42 is rotated, the ball plunger 61 comes into contact with one of the detents 77, alerting the user that the selection pin 60 is aligned with one of the quadrants and puller wire anchors 42. If desired, the detents 77 can have different shapes or sizes to provide a different feel to the user for each detent so that the user can distinguish between the puller wire anchors 42 when rotating the sleeve 44.

In the above-described embodiment, the catheter has four puller wires 31, and thus all four of the slidable puller wire anchors 42 are provided in an "active" position. In other words, all four of the anchors 42 are assembled to permit movement of any of the anchors by the selection pin 60. If desired, the catheter can comprise less than four puller wires 31, e.g., can be unidirectional with a single puller wire, bidirectional with two puller wires, or can be tridirectional with three puller wires. If less than for puller wires 31 are used, it is unnecessary to have all four puller wire anchors 42 active. Accordingly, the unused puller wire anchors are put into a "disabled" position.

The design of the present invention provides for two different "disabled" positions, an active disabled position and a passive disabled position. A puller wire anchor 42 is in an active disabled position when it blocks rotational movement of the selection pin 60 and sleeve 44, and is in a passive disabled position when it is not longitudinally slidable, but does not block rotational movement of the selection pin and sleeve. To place an active puller wire anchor 42 (see 42A) in an active disabled position, the puller wire anchor is first flipped upside-down (see 42B) so that its closed end 46 is facing distally. In other words, the V-shaped groove 48 is inverted so that the selection pin 60 cannot slide into the groove. The puller wire anchor 42 is then removably fixed in place relative to the barrel 70 so that a portion of the anchor extends beyond the distal end of the barrel. As a result, the fixed puller wire anchor 42 blocks the selection pin 60 from rotating 360 degrees, limiting the rotation to only 270 degrees. If only two puller wires 31 are used, two adjacent puller wire anchors 42 can be actively disabled, thereby limiting rotation of the selection pin 60 to 180 degrees. If only one puller wire 31 is used, three puller wire anchors 42 can be actively disabled, thereby restricting the position of the selection pin 60 to a single quadrant.

To place a puller wire anchor 42 in a passive disabled position, the anchor is similarly inverted and then removably fixed in place relative to the barrel 70 so that the distal end of the anchor is generally level with or proximal to the distal end of the barrel. As a result, the fixed puller wire anchor does not limit rotation of the selection pin 60 and sleeve 44. The choice of active or passive disablement will depend on the preference of the user. The inventive design permits a catheter with uniform pieces or components, whereby the catheter design can be modified during manufacturing to meet the user's needs and preferences without requiring that different components be used.

In the depicted embodiment, a puller wire anchor 42 is removably fixed in place relative to the barrel 70 using a fixation pin (not shown). Specifically, fixation holes 79 are provided at the distal end of the outer wall of the barrel 70. The disabled puller wire anchor 42 is mounted in the distal end of the barrel 70 by inserting the fixation pin through one of the barrel fixation holes 79 and one of the mounting holes 49 on that anchor. The choice of fixation hole 79 and mounting hole 49 will depend on whether the puller wire anchor 42 is to be actively disabled or passively disabled. For example, if the anchor 42 is to be actively disabled, the fixation hole 79 and mounting hole 49 are selected such that the distal end of the anchor extends beyond the distal end of the barrel 70.

A preferred means for anchoring a puller wire 31 to the puller wire anchor 42 comprises a short piece of hypodermic stock (not shown) that is fixedly attached, e.g., by crimping, to the proximal end of the puller wire after it has passed through the puller wire hole 51 in the anchor. The hypodermic stock has a diameter greater than the diameter of the puller wire hole 51 and thus prevents the proximal end of the puller wire 31 from being pulled distally through the anchoring hole. As an alternative, a cross-member (not shown), e.g., stainless steel ribbon, may be welded to the proximal end of the puller wire 31 such that the cross-member prevents the puller wire from being pulled through the puller wire hole 51 of the anchor 42. It is understood that any other suitable mechanism for anchoring the proximal end of a puller wire 31 to a puller wire anchor 42 may be used.

In the embodiment described above, the central lumen 18 is used for passage of electrode lead wires 36. It is understood that the central lumen 18 may be omitted, if desired. In such an embodiment, one or more the off-axis lumens 17 must be sufficiently large to carry the electrode lead wires 36 in addition to the compression coil 33 and the puller wire 31. In such an embodiment, each compression coil 33 is preferably covered by a non-conductive sheath (not shown) to prevent electrical contact with the lead wires 36. Moreover, preferably a tunnel is be in each of the glue joints securing the proximal and distal ends of the compression coil to the catheter body. The tunnels provide means for passage of the electrode lead wires through the glue joints. Such a tunnel may be formed, for example, by short pieces of polyimide tubing or the like. Alternatively, if the lead wires 36 are carried in one or more of the off-axis lumens 17, the central lumen 18 may be used as a delivery route for fluids, solids, devices, and the like (e.g., pharmaceutical compounds, growth factors, hormones, gene therapy vectors, angiography tracer substances, or angioplasty devices), or as a means for collecting tissue or fluid samples. As would be recognized by one skilled in the art, other catheter designs could be provided for use with the control handle described above. In another alternative embodiment, a single central lumen is provided in the catheter body 12, with the lead wires 36, puller wires 31 and compression coils 33 all extending through the single lumen.

If desired, the sectioned insert 64 can be modified to provide a different number of sections depending on the number of puller wires 31 in the catheter. For example, the sectioned insert 64 can have only two fins 67, thereby forming halves rather than quadrants. With such a design, only two puller wire anchors 42 would be provided, and each would preferably have a generally semi-circular cross-section to fit into the halves of the sectioned insert 64. Alternatively, the sectioned insert 64 could have three fins or five fins. In another alternative embodiment, the sectioned insert 64 could be replaced with an insert that has only one region in which a single puller wire anchor 42 is slidable, or the insert could be eliminated altogether. In only a single puller wire anchor 42 is provided, it is not necessary that the sleeve 42 and selection pin 60 be rotatable.

As would be recognized by one skilled in the art, the selection pin 60 described herein does not necessarily have to be in the form of a pin, i.e., a cylindrically-shaped device. The selection pin 60 can be provided in any shape, size or form that permits the pin to be attached (permanently or removably) to the sleeve 44 and is capable of moving a puller wire anchor 42 proximally upon pushing the selection pin 60 proximally to contact the anchor. Preferably the selection pin 60 is of a suitable size and shape such that it contacts only one puller wire anchor 42 at a time. However, where only one puller wire anchor 42 is provided, the selection pin 60 can be of any suitable shape that fits within the handle body 40.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. Accordingly, the foregoing description should not be read as pertaining only to the precise structures described and illustrated in the accompanying drawings, but rather should be read consistent with and as support to the following claims which are to have their fullest and fair scope.

What is claimed is:

1. A deflectable catheter comprising:
    an elongated, flexible tubular catheter body having proximal and distal ends and a lumen extending therethrough;
    a control handle at the proximal end of the catheter body, the handle comprising:
        a handle body having proximal and distal ends and comprising an outer wall and a generally hollow interior, wherein the proximal end of the catheter body is fixedly attached to the handle body,
        a slidable puller wire anchor longitudinally movable within the interior of the handle body relative to the handle body and catheter body,
        a sleeve slidably mounted on the exterior of the handle body, and
        a selection pin fixedly attached to the sleeve and extending into the interior of the handle body proximal to the slidable puller wire anchor,
    whereby, in use, proximal movement of the sleeve and selection pin relative to the handle body causes the selection pin to contact the slidable puller wire anchor and move the slidable puller wire anchor proximally relative to the handle body and catheter body; and
    a puller wire having proximal and distal ends and extending through the lumen of the catheter body and into the control handle, wherein the proximal end of the puller wire is anchored to the slidable puller wire anchor and the distal end of the puller wire is anchored in the distal end of the catheter body, whereby, in use, proximal movement of the slidable puller wire anchor relative to the catheter body results in deflection of the catheter body.

2. A catheter according to claim 1, wherein the sleeve is rotatably mounted on the handle body.

3. A catheter according to claim 1, wherein the handle body includes a longitudinal slot in the outer wall for receiving the selection pin, whereby, in use, proximal movement of the selection pin causes the selection pin to slide proximally in the longitudinal slot.

4. A catheter according to claim 1, wherein the catheter comprises a plurality of puller wires and a plurality of puller wire anchors.

5. A catheter according to claim 4, wherein the handle body comprises:
    a barrel at the handle body's proximal end, the barrel having proximal and distal ends, an outer wall, and a generally hollow interior;
    a nose piece at the handle body's distal end, the nose piece having proximal and distal ends, an outer wall, and a generally hollow interior;
    a sectioned insert permanently or removably mounted, at least in part, in the distal end of the barrel and permanently or removably attached to the nose piece, wherein the sectioned insert comprises an axis and a plurality of fins extending from the axis, thereby forming a plurality of sections, wherein one of the plurality of puller wire anchors is provided in each of the sections.

6. A catheter according to claim 5, wherein the sectioned insert comprises four fins located at 90 degree angles relative to one another, and wherein the handle comprises four puller wire anchors.

7. A catheter according to claim 6, wherein the catheter comprises four puller wires.

8. A catheter according to claim 6, wherein the catheter comprises less than four puller wires.

9. A catheter according to claim 6, wherein the handle body has four longitudinal slots in the outer wall for receiving the selection pin, each longitudinal slot corresponding in position to one of the four quadrants formed by the sectioned insert.

10. A catheter according to claim 5, wherein the sectioned insert has a threaded distal section distal to the fins for removably attaching the sectioned insert to the nose piece.

11. A catheter according to claim 10, further comprising a central groove between the threaded distal section and the fins, whereby the central groove is sized to accomodate the selection pin such that, in use, the selection pin can be rotated within the central groove.

12. A catheter according to claim 5, wherein the sectioned insert comprises a circumferential ridge distal the fins and a central groove between the circumferential ridge and the fins, whereby the central groove is sized to accomodate the selection pin such that, in use, the selection pin can be rotated within the central groove.

13. A catheter according to claim 5, wherein:

the distal end of the nose price comprises a plurality of compressible sections with longitudinal slits therebetween arranged in a generally-cylindrical relationship;

the handle body further comprises an end cap that is mounted on the distal end of the nose piece; and the catheter body extends into the nose piece between the compressible sections, whereby the end cap mounted on the distal end of the nose piece compresses the compressible sections against the catheter body, thereby holding the catheter body tightly in place.

14. A deflectable catheter comprising:

an elongated, flexible tubular catheter body having proximal and distal ends and a lumen extending therethrough;

a control handle at the proximal end of the catheter body, the handle comprising:

a handle body having proximal and distal ends and comprising:

a barrel at the handle body's proximal end, the barrel having proximal and distal ends, an outer wall having a plurality of longitudinal slots therein, and a generally hollow interior, a nose piece at the handle body's distal end, the nose piece having proximal and distal ends, an outer wall, and a generally hollow interior, and a sectioned insert permanently or removably mounted, at least in part, in the distal end of the barrel and permanently or removably attached to the nose piece, wherein the sectioned insert comprises an axis, a plurality of fins extending from the axis, thereby forming a plurality of sections, and a central groove distal to the fins, wherein the longitudinal slots in the outer wall of the barrel correspond in number and location to the sections formed by the sectioned insert;

a plurality of slidable puller wire anchors, wherein each puller wire anchor is provided in one of the sections of the sectioned insert and longitudinally movable within the interior of the handle body relative to the handle body and catheter body;

a sleeve slidably and rotatably mounted on the exterior of the handle body; and a selection pin fixedly attached to the sleeve and extending into the interior of the handle body proximal to the slidable puller wire anchor; whereby, in use, rotation of the sleeve relative to the handle body causes the selection pin to rotate within the central groove, and further wherein proximal movement of the sleeve and selection pin relative to the handle body causes the selection pin to contact one of the slidable puller wire anchors and move that slidable puller wire anchor proximally relative to the handle body and catheter body; and a puller wire having proximal and distal ends and extending through the lumen of the catheter body and into the control handle, wherein the proximal end of the puller wire is anchored to one of the slidable puller wire anchors and the distal end of the puller wire is anchored in the distal end of the catheter body, whereby, in use, proximal movement of the slidable puller wire anchor attached to the puller wire relative to the catheter body results in deflection of the distal end of the catheter body.

15. A catheter according to claim 14, comprising a plurality of puller wires having proximal and distal ends and corresponding in number to the number of puller wire anchors, wherein the proximal end of each puller wire is anchored to a corresponding puller wire anchor.

* * * * *

UNITED STATES PATENT AND TRADEMARK OFFICE
CERTIFICATE OF CORRECTION

PATENT NO. : 6,571,131 B1  Page 1 of 1
DATED : May 27, 2003
INVENTOR(S) : Frank Nguyen It is certified that error appears in the above-identified patent and that said Letters Patent is hereby corrected as shown below:

Title page,
Item [57], ABSTRACT,
Line 2, replace "pfor" with -- for --
Line 27, replace "cather" with -- catheter --

Column 13,
Lines 23 and 29, change "accomodate" to -- accommodate --
Line 33, change "price" to -- piece --

Signed and Sealed this

Fifth Day of October, 2004

JON W. DUDAS
*Director of the United States Patent and Trademark Office*